United States Patent [19]

Towne et al.

[11] Patent Number: 5,059,177
[45] Date of Patent: Oct. 22, 1991

[54] TRIPLE LUMEN BALLOON CATHETER

[75] Inventors: Randall Towne, Maryville, Tenn.; Raul Alcebo, Wallingford; Ricardo Cordido, Hamden, both of Conn.

[73] Assignee: Cordis Corporation, Miami Lakes, Fla.

[21] Appl. No.: 510,970

[22] Filed: Apr. 19, 1990

[51] Int. Cl.$^5$ ............................................. A61M 29/00
[52] U.S. Cl. ..................................... 604/96; 128/657; 128/772; 606/194
[58] Field of Search ............................... 604/96–103, 604/280, 283; 606/191–194; 128/657, 772

[56] References Cited

U.S. PATENT DOCUMENTS

| | | | |
|---|---|---|---|
| 329,354 | 5/1903 | Loewenstein | 604/96 |
| 3,995,623 | 12/1976 | Blake | 604/21 |
| 4,273,131 | 6/1981 | Olsen | 606/191 |
| 4,664,113 | 5/1987 | Frisbie et al. | 604/96 |
| 4,944,740 | 7/1990 | Buchbinder | 606/194 |
| 4,960,411 | 10/1990 | Buchbinder | 128/657 |
| 4,983,167 | 1/1991 | Sahota | 604/96 |

FOREIGN PATENT DOCUMENTS

| | | | |
|---|---|---|---|
| 8801885 | 3/1988 | World Int. Prop. O. | 128/657 |
| 0303756 | 2/1989 | World Int. Prop. O. | 604/96 |

Primary Examiner—C. Fred Rosenbaum
Assistant Examiner—Chalin Smith
Attorney, Agent, or Firm—Gerstman & Ellis, Ltd.

[57] ABSTRACT

A balloon catheter, preferably of the float-advancement type, defines a balloon carried adjacent the catheter distal end and a first catheter lumen communicating between the balloon at a proximal catheter location. By this invention, second and third, separate catheter lumens extend between proximal and distal catheter locations and are open at each end. The second and third catheter lumens are each proportioned to receive a catheter advancement guidewire to permit installation of a pair of the guidewires at desired body locations. Preferably, the second and third lumens define distal open ends which are longitudinally spaced from each other.

6 Claims, 1 Drawing Sheet

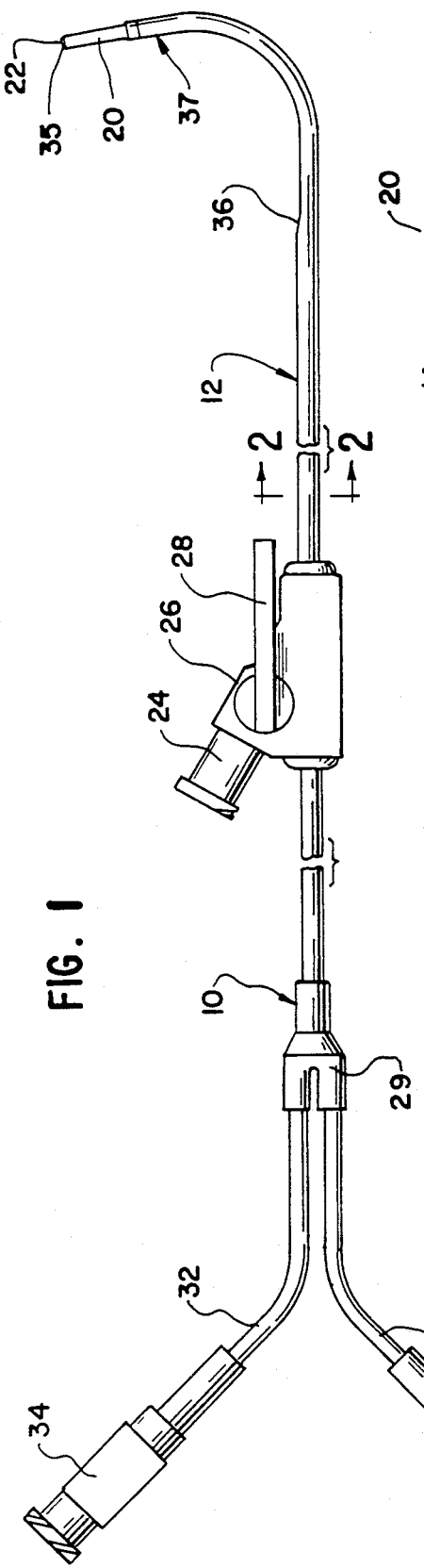
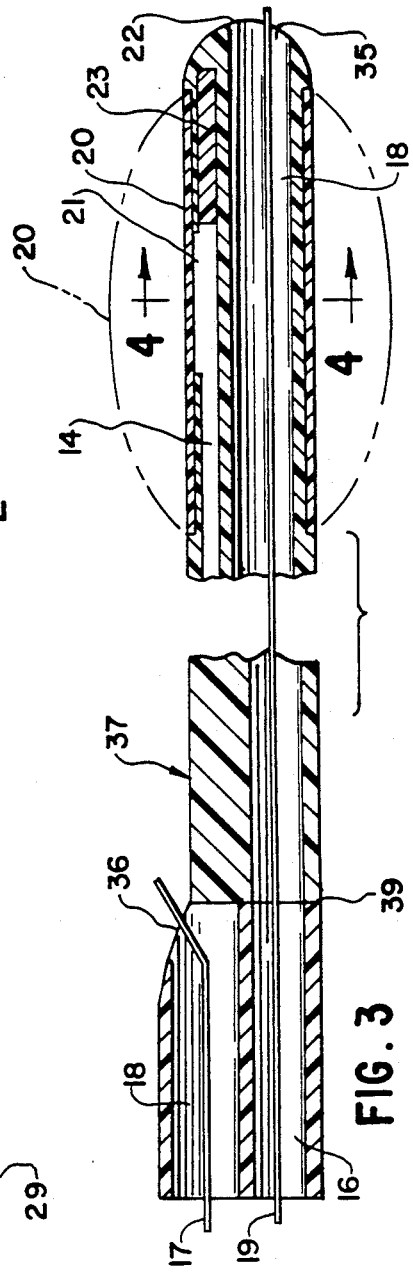
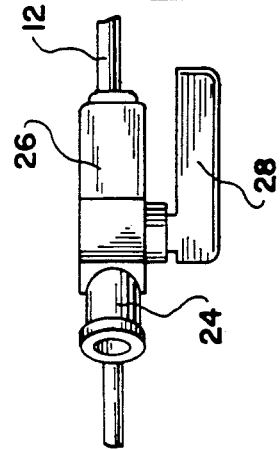
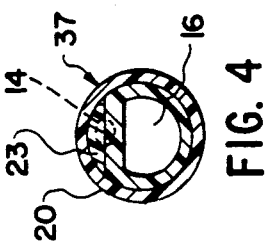
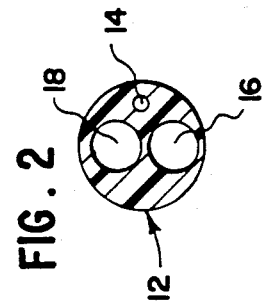

TRIPLE LUMEN BALLOON CATHETER

BACKGROUND OF THE INVENTION

Dilatation balloon catheters are known for use in valvuloplasty procedures, which are performed with respect to heart valves for purposes of dilatation to remove calcification and the like. Such catheters are also used to expand occluded arteries.

It is also known to emplace a catheter into its desired position in the heart by the procedure of float-advancement, in which a balloon is inflated near the distal tip of the catheter, after the catheter has been inserted into an appropriate blood vessel that leads toward the desired site of emplacement. Then, the inflated catheter balloon acts rather like a sail on a boat, being swept along by the stream of blood in the blood vessel, and thus carrying the catheter through the arteriovenous system of the patient into its desired position. When the desired position is reached, the balloon is deflated once again.

Thereafter, in the prior art a guidewire may be inserted through a separate catheter lumen which is open at both ends and extending through the catheter, for emplacement of the guidewire. Then, the float-advancement balloon catheter may be withdrawn, while leaving the guidewire in position, and a separate valvuloplasty catheter may be advanced along the guidewire into its desired position for the valvuloplasty procedure.

In the prior art it is often desired to insert a second valvuloplasty catheter through the same path within the arteriovenous system, so that its distal tip occupies a somewhat different location from the first catheter. For example, a pair of dilatation catheters may be provided in a valvuloplasty procedure to be positioned on opposite sides of a heart valve, for example the mitral valve. This has been accomplished up to the present time by repeating the process described above, using another float-advancement balloon catheter, followed by advancement of the guidewire through a lumen of the catheter once the balloon catheter has been properly positioned. Then, the float-advancement type balloon catheter may be removed, and a second valvuloplasty balloon catheter may be advanced along the second guidewire.

The above procedure exhibits the significant disadvantage that four catheters are required to obtain emplacement of two catheters in desired positions for a valvuloplasty procedure. Each of these catheters must be separately advanced into the patient, which increases the severity and challenge of the procedure.

In accordance with this invention, similar results may be obtained to the above procedure, with the elimination of one of the four catheters described above. Additionally, by this invention, easy monitoring of pressures on both sides of a heart valve may be obtained prior to advancement of the guidewires through the catheter.

DESCRIPTION OF THE INVENTION

In this invention a balloon catheter is provided which defines a catheter shaft, and a balloon carried adjacent the catheter shaft distal end. A first catheter lumen communicates through the catheter shaft between the balloon and a proximal catheter location. Communication with the balloon may be made at this proximal location by conventional means for pressurizing and depressurizing the balloon while it is emplaced within the body.

By this invention, second and third catheter lumens, separate from each other and the first lumen, are defined in the catheter shaft, with the second and third lumens extending between proximal and distal catheter locations. The second and third lumens are open at each end, and are each proportioned to receive a catheter advancement guidewire. Thus, by this invention, the one catheter can provide installation of a pair of guidewires at desired body locations after the balloon catheter described above has been positioned at a desired body site.

The catheter of this invention may be emplaced, and the second and third catheter lumens may be used for coordinated pressure monitoring at spaced sites. For example the spaced sites, which are at the distal openings of the second and third catheter lumens, may be positioned on opposite sides of a heart valve to determine pressure differential data.

It is preferred for the balloon catheter of this invention to be proportioned and adapted to be of the float-advancement type as described above, in which the balloon may be inflated to cause the catheter to be advanced along with the blood flow in a blood vessel toward its desired site of positioning. Preferably, the second and third lumens define their distal, open ends at positions which are longitudinally spaced from each other, so that each of the open ends may be positioned on a side of a heart valve which is opposed to the open end of the other of the second and third lumens. However, alternatively, the second and third lumens may terminate with their distal ends longitudinally close to each other although, typically in that circumstance, on opposed sides of the catheter.

It is also preferred for the diameter of the catheter portion between the second and third lumen distal open ends which are longitudinally spaced from each other to be less than the diameter of the catheter portion which is proximal to both of the second and third lumen distal open ends. This is possible since, when one of the second and third lumens terminate, it is possible for the remaining catheter portion distal to that location to be of less diameter, which facilitates the entry of the catheter into narrow blood vessels and the like.

Then, when the catheter of this invention is properly positioned with its distal tip, for example, passing through a heart valve so that the second and third lumen distal ends are located on opposite sides of the valve, a pair of guidewires may be inserted through the respective second and third lumens to advance the guidewires to their desired positions. Then, the balloon catheter of this invention may be withdrawn, and conventional valvuloplasty dilatation catheters, for example, are respectively advanced along each of the guidewires, to position the catheters for the desired valvuloplasty procedure, or for any other appropriate medical procedure.

The catheter may be conventionally equipped with radiopaque markers as desired, and also with a valve controlling fluid flow through the first lumen, so that the balloon may be inflated or deflated as desired. Thus, after positioning of the guidewires, the catheter of this invention is removed and replaced with dilatation catheters, which may be stronger, less flexible, and more capable of withstanding high pressures. The dilatation catheters are then advanced along the emplaced guidewires for positioning in the ventricle or aorta.

DESCRIPTION OF THE DRAWINGS

In the drawings, FIG. 1 is a plan view of a float-advancement type catheter made in accordance with this invention.

FIG. 2 is a sectional view taken along line 2—2 of FIG. 1;

FIG. 3 is an enlarged, longitudinal sectional view of the distal tip of the catheter of FIG. 1, but rotated 90° about its longitudinal axis;

FIG. 4 is a sectional view taken along line 4—4 of FIG. 3 with the distal portion thereof shown to be rotated 90° relative to the proximal portion; and FIG. 5 is a fragmentary view of a portion of the catheter of FIG. 1, but rotated 90° about its longitudinal axis.

DESCRIPTION OF SPECIFIC EMBODIMENTS

Referring to the drawings, catheter 10 may be a relatively flexible balloon catheter of the type which is commercially available and used for float-advancement, except as otherwise indicated herein. Catheter 10 defines a catheter shaft 12 which includes first lumen 14, second lumen 16 and third lumen 18. As shown, first lumen 14 may be somewhat smaller in diameter than the other two lumens.

First lumen 14 communicates with a balloon 20 near the distal end 22 of catheter 10, through aperture 21. First lumen 14 communicates at its other end with inflation port 24 which passes through valve member 26 which is controlled by handle 28, so that the balloon may be inflated and deflated with a conventional syringe, and held in inflated condition, by appropriate use of valve 26. A plug portion 23 may be added to strengthen distal end 22.

At its proximal end, catheter shaft 12 communicates with a Y connector 29, with lumen 16 communicating with connection tube 30 and lumen 18 communicating with connection tube 32. These tubes are equipped at their proximal ends with connectors 34 of conventional design which may serve to receive guidewires which, after the catheter has been emplaced in the body of the patient in the proper position, may respectively advance through lumens 16, 18 into desired positions.

Lumen 16 extends to the distal end 22 of the catheter and defines an open port 35 there. On the other hand, lumen 18 encounters an open port 36 at a position proximal to the distal end, so that the distal port 35 of lumen 16 is longitudinally spaced from the distal port 36 of lumen 18. Thus, the catheter may be advanced so that the respective ports 35, 36 are positioned on opposite sides of a heart valve, or in any other appropriate part of the body.

Distal tip portion 37 of the catheter may be preformed and conventionally sealed at seal area 39 to the rest of catheter 10.

In use, catheter 10 is advanced by inflating balloon 20 as shown in dotted lines in FIG. 3, after typically at least the distal tip portion 37 of the catheter has been emplaced in a desired artery or vein. Then, the flow of blood within the artery or vein catches the balloon and sweeps it along, drawing the catheter into the body as the balloon is advanced. When the distal tip portion 37 of the catheter reaches its desired position, as determined for example by a fluoroscope observing radiopaque markings on the catheter, the forward motion of the catheter may be halted and the balloon deflated.

At this point, pressures may be measured through the open lumens 16, 18. Particularly, the pressure differential across a heart valve such as the mitral valve may be measured if the catheter is positioned so that its distal end 22 passes through the mitral valve while port 36 remains on the other side thereof.

When the desired pressure data has been obtained, a guidewire 17, 19 may be advanced through each of lumens 16, 18 until the distal end of one guidewire typically projects out of port 35 and the distal end of the other guidewire projects out of port 36. When the guidewires are positioned to the satisfaction of the surgeon, catheter 10 may be withdrawn from the system, leaving the guidewires in position.

Thus, two positioned guidewires have been provided, making use of only a single catheter rather than the two catheters of the prior art. This of course provides significant savings in cost and convenience, and it also provides a procedure that is less damaging to the cardiovascular system of the patient.

Following this, the desired dilatation catheters may be advanced along the respective guidewires in a manner similar to the prior art, for completion of the valvuloplasty procedure.

Typically, a catheter in accordance with this invention may be a French size 7.5 to 8 at its maximum, being on the order of 110 centimeters in length. Distal tip 37 may be of French size 7 in this case, but the catheter may be of any desired diameters. The second and third lumens may be proportioned to receive a guidewire having a diameter of 0.038 inch, for example. Such a lumen diameter may be about 0.042 inch.

The above has been offered for illustrative purposes only, and is not intended to limit the scope of the invention of this application, which is as defined in the claims below.

That which is claimed is:

1. In a balloon catheter which defines a catheter shaft, and a balloon carried adjacent the catheter shaft distal end; a first catheter lumen communicating through the shaft between the balloon and a proximal catheter location, the improvement comprising, in combination:

second and third separate catheter lumens extending through the shaft between proximal and distal catheter locations and open at each end, said second and third catheter lumens each carrying a catheter advancement guidewire, each guidewire being free of attachment to said catheter, to permit installation of said guidewires at desired body locations.

2. The balloon catheter of claim 1 which is proportioned and adapted to be of the float-advancement type.

3. The balloon catheter of claim 1 in which the second and third lumens define distal open ends which are longitudinally spaced from each other.

4. The balloon catheter of claim 3 in which the diameter of the catheter portion between the second and third lumen distal open ends is less than the diameter of the catheter portion which is proximal to both of the second and third lumen distal open ends.

5. In a balloon catheter of the float-advancement type which defines a catheter shaft, and a balloon carried adjacent the catheter shaft distal end; a first catheter lumen communicating through the shaft between the balloon and a proximal catheter location, the improvement comprising, in combination:

second and third separate catheter lumens extending through the shaft between proximal and distal catheter locations and open at each end, said second and third catheter lumens each carrying a catheter advancement guidewire, each guidewire being free of attachment to said catheter, to permit installation of said guidewires at desired body locations, in which the second and third lumens define distal open ends which are longitudinally spaced from each other.

6. The balloon catheter of claim 5 in which the diameter of the catheter portion between the second and third lumen distal open ends is less than the diameter of the catheter portion which is proximal to both of the second and third lumen distal open ends.

* * * * *